United States Patent
Kang et al.

(10) Patent No.: US 7,491,262 B2
(45) Date of Patent: Feb. 17, 2009

(54) SILVER NANOPARTICLE/POLYMER NANOCOMPOSITE MEMBRANES FOR OLEFIN/PARAFFIN SEPARATION AND METHOD OF PREPARING THE SAME

(75) Inventors: Yong Soo Kang, Seoul (KR); Kook Heon Char, Seoul (KR); Sang Wook Kang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 497 days.

(21) Appl. No.: 11/290,889

(22) Filed: Nov. 29, 2005

(65) Prior Publication Data
US 2007/0012189 A1    Jan. 18, 2007

(30) Foreign Application Priority Data
Jul. 12, 2005    (KR) ................ 10-2005-0062641

(51) Int. Cl.
  *B01D 53/22*    (2006.01)
(52) U.S. Cl. .............. 96/11; 96/4; 96/12; 96/13; 96/14; 95/45; 95/50; 427/595; 427/212; 427/216; 427/245; 427/372.2
(58) Field of Classification Search ............. 96/4, 96/11, 12, 13, 14; 95/45, 50, 54; 427/595, 427/127, 212, 213, 216, 245, 372.2; 429/33
See application file for complete search history.

(56) References Cited

U.S. PATENT DOCUMENTS

| | | | | |
|---|---|---|---|---|
| 4,919,694 A | * | 4/1990 | Hata et al. | 96/12 |
| 5,102,547 A | | 4/1992 | Waite et al. | |
| 5,104,428 A | * | 4/1992 | Doi et al. | 96/14 |
| 5,354,474 A | | 10/1994 | LaPack et al. | |
| 5,670,051 A | | 9/1997 | Pinnau et al. | |
| 6,517,611 B1 | * | 2/2003 | Kuznicki et al. | 95/50 |
| 6,899,744 B2 | * | 5/2005 | Mundschau | 96/12 |
| 7,264,650 B2 | * | 9/2007 | Lou et al. | 96/4 |

FOREIGN PATENT DOCUMENTS

| | | |
|---|---|---|
| EP | 1 388 561 | 2/2004 |
| EP | 1 552 875 | 7/2005 |
| JP | 61-278330 | * 12/1986 |

* cited by examiner

*Primary Examiner*—Jason M Greene
(74) *Attorney, Agent, or Firm*—Jones Day

(57) ABSTRACT

There is provided a nanocomposite membrane comprising an Ag-nanoparticle/polymer nanocomposite, in which the Ag-particles are uniformly dispersed in the polymer matrix, and a support membrane for supporting the nanocomposite, as well as a process of preparing said membrane. The nanocomposite membrane of the present invention comprising a neutral Ag-nanoparticle as an olefin carrier, which is chemically stable, has excellent long-term operation performance characteristics as well as high selectivity and permeability. Thus, it can be advantageously used for the separation of olefin from an olefin/paraffin mixture.

8 Claims, 1 Drawing Sheet

SILVER NANOPARTICLE/POLYMER NANOCOMPOSITE MEMBRANES FOR OLEFIN/PARAFFIN SEPARATION AND METHOD OF PREPARING THE SAME

FIELD OF THE INVENTION

The present invention is directed to a nanocomposite membrane for olefin/paraffin separation and a process of preparing the same. The nanocomposite membrane of the present invention has improved long-term operation performance characteristics as well as high permeability and selectivity for olefins.

BACKGROUND OF THE INVENTION

Olefins are primarily generated by heat degradation of naphtha at a high temperature, which is a by-product obtained from a petroleum refining process. Since olefins, which are industrially important and serve as the basis of the petrochemical industry, are commonly produced together with paraffins such as ethane and propane, the techniques for separating the two are very important in the relevant industries.

A typical distillation method has been widely employed for separating a mixture of olefin/paraffin, such as ethylene/ethane and propylene/propane. However, since the molecular size and physical properties (e.g., relative volatility) of olefin are similar to those of paraffin, the separation of the two requires tremendous resources in terms of equipment and energy.

For example, the distillation method currently used in the art needs to operate a distillation column, which has about 120 to 160 stages, at a low temperature of −30° C. and a high pressure of about 20 Pa for the separation of ethylene/ethane. Further, such distillation method runs a distillation column, which has about 180 to 200 stages, at a low temperature of −30° C. and a several pressure with a reflux ratio of over 10 for the separation of propylene/propane. Therefore, there is a need to develop a new method of separating alkene/alkane hydrocarbons that can substitute the conventional distillation method.

As an alternative method for the conventional distillation method, a separation method using a membrane has been suggested. The membrane technique has made significant progresses during past several decades in separating gaseous mixtures such as nitrogen/oxygen, nitrogen/carbon dioxide and nitrogen/methane.

However, the typical gaseous separation membrane does not usually succeed in separating the mixture of olefin/paraffin hydrocarbons due to their similar molecular and physical properties. As a membrane showing high separation efficiency for the olefin/paraffin mixture, a facilitated transport membrane, which is based on a different concept from the typical gaseous membrane, has been developed.

The separation of a mixture using a membrane is accomplished by using the difference in permeability of each ingredient consisting the mixture. Most membrane materials show an inverse correlation between permeability and selectivity, which results in limiting their application. However, if a facilitated transport phenomenon is applied to the membrane technique, it will be possible to simultaneously increase the permeability and selectivity, thus enlarging its range of application. When the membrane contains a carrier capable of reacting selectively and reversibly with a specific ingredient in the mixture, an additional mass transport occurs due to a reversible reaction between the carrier and the specific ingredient. This results in increasing the efficiency of the whole mass transport. Therefore, the whole mass transport can be described as a sum of mass transport according to the Fick's law, which is caused by the reversible reaction of the carrier. This phenomenon is referred to as facilitated transport.

A supported liquid membrane, which is one of the membranes formed by employing the concept of facilitated transport, has been developed. The supported liquid membrane is prepared by dissolving a carrier capable of promoting the mass transfer in a solvent (e.g., water) and filling a porous membrane with the resulting solution. Such supported liquid membrane is generally successful.

For example, the Steigelmann and Hughes references (U.S. Pat. Nos. 3,758,603 and 3,758,605, respectively) disclose a supported liquid membrane, wherein the selectivity for ethylene/ethane ranges from 400 to 700 and the permeability to ethylene is 60 GPU (1 GPU=$1\times10^{-6}$ $cm^2$ (STP)/$cm^2 \cdot sec \cdot cmHg$). Such permeable separation efficiencies are considered to be satisfactory. However, since such supported liquid membrane applies the facilitated transport efficiency only under a wet condition, it is not possible to maintain high permeable separation efficiency during a long-term operation due to the eventual loss of the solvent and the lowering of the separation efficiency.

In order to solve the above problem associated with the supported liquid membrane, U.S. Pat. No. 4,318,714 issued to Kimura, et al. discloses an ion-exchange membrane exhibiting facilitated transport of a certain gas by attaching a suitable counter-ion to the ion-exchange membrane matrix, which reacts reversibly with the gas to be separated. However, such ion-exchange membrane exhibits the facilitated transport property only under a wet condition similar to the supported liquid membranes described in the Steigelmann and Hughes references.

U.S. Pat. Nos. 5,015,268 and 5,062,866 disclose polymeric membranes for separating aliphatically unsaturated hydrocarbons from hydrocarbon mixtures. The polymeric membrane comprises a hydrophilic polymer such as a polyvinylalcohol, which contains metals capable of being in complex with the aliphatically unsaturated hydrocarbons. However, such polymeric membranes can exhibit satisfactory separation efficiency only when a feed stream is saturated with steam by bubbling it with water before contacting the membrane or swelling the membrane by using ethylene glycol or water.

All exemplary membranes described above must be maintained under a humidified condition so that they contain water or a similar solvent. In case of utilizing these membranes for the separation of a dry hydrocarbon gaseous mixture (e.g., olefin/paraffin) having no solvent such as water, solvent loss is inevitable. Thus, there has been developed a method for supplementing a solvent periodically in order to keep the membrane at a constant wet condition. However, it is impossible to apply such method in a practical manner and the prepared membranes are typically unstable.

U.S. Pat. No. 4,614,524 issued to Kraus, et al. describes a water-free immobilized liquid membrane for facilitated transport of aliphatically unsaturated hydrocarbons. The membranes are prepared by chemically bonding transition metal ions to a semi-permeable ion exchange membrane (e.g., Nafion) and are then plasticized by treatment with glycerol. However, their selectivity for a dry ethylene/ethane mixture is too low (i.e., about 10 under ambient condition) for practical use. Further, the plasticizer becomes lost with time and the membrane shows no selectivity when it does not undergo plasticization.

As described above, the conventional polymeric membranes cannot separate the mixture of olefin/paraffin hydrocarbons having similar molecular and physical properties. Thus, there has been a need to develop a facilitated transport membrane capable of selectively separating olefin from the mixture. However, the conventional transport membranes have to maintain the activity of their carriers by employing several methods such as filling a porous membrane with a carrier-containing solution, adding a volatile plasticizer, saturating a feed gas with steam and the like. Further, these facilitated transport membranes are not practical since their constituents become lost over time, thus deteriorating the stability of the membrane. In addition, the liquid solvent, which is provided periodically to the membrane in order to maintain its activity, has to be removed from the final product.

Recently, there have been also developed solid polymer electrolyte membranes containing a carrier complex in the form of an ionic metal salt, which is dissolved not in water or other solvent but in a solid polymer (see U.S. Pat. No. 5,670,051 issued to Pinnau, et al.; and Korean Patent No. 315896 issued to the present inventors). The solid polymer electrolyte membranes can be prepared, e.g., by coating a solid polymer electrolyte consisting of a transition metal salt such as $AgBF_4$ and a polymer such as a poly(2-ethyl-2-oxazole) (POZ) having an amide group allowing the metal ion to be coordinated, on a porous support. This solid polymer electrolyte membrane (e.g., an $AgBF_4$/POZ membrane) shows a high initial selectivity of 50 or more for the separation of olefin from an olefin/paraffin mixture. However, there is a problem in that the silver ion adopted as a carrier in the membrane has a tendency of being reduced to $Ag^0$-particles undergoing agglomeration by themselves, thereby continuously decreasing the selectivity of the membrane over time. Further, the silver ion is chemically unstable to easily react with a sulfur-containing compound, acetylene or a hydrogen gas, etc., which generally exists in a dry hydrocarbon gas mixture, to lose its activity as a facilitated transport carrier for olefins.

Therefore, there is a need to develop a membrane for olefin/paraffin separation, which comprises chemically stable olefin carrier, thereby being able to maintain its activity over a long operational time under dry feed gaseous conditions.

SUMMARY OF THE INVENTION

It is a primary object of the present invention to provide a membrane having excellent long-term operation performance characteristics as well as high permeability and selectivity for olefins.

It is another object of the present invention to provide a method of preparing such a membrane.

In accordance with one aspect of the present invention, there is provided a nanocomposite membrane for separation of olefin from an olefin/paraffin mixture, comprising an Ag-nanoparticle/polymer nanocomposite and a porous supported membrane for supporting the nanocomposite.

In accordance with another aspect of the present invention, there is provided a process for preparing said membrane, comprising the steps of: (i) providing an Ag-nanoparticle coated with a coating agent; (ii) dispersing the surface-coated Ag-nanoparticle in a polymer solution to obtain a nanocomposite solution; and (iii) coating the nanocomposite solution on a porous support membrane.

BRIEF DESCRIPTION OF THE DRAWINGS

The above and other objects of the present invention will become apparent from the following description of preferred embodiments given in conjunction with the accompanying drawing, in which.

DETAILED DESCRIPTION OF THE PREFERRED EMBODIMENTS

Figure 1:
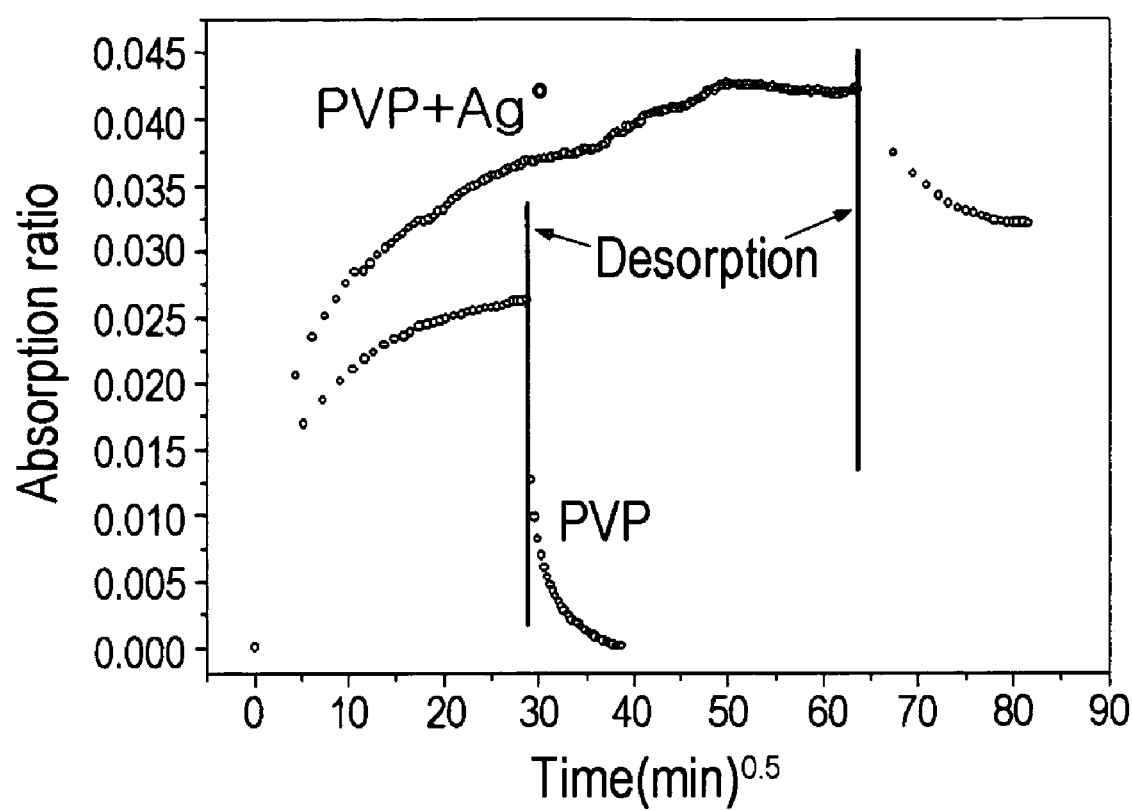
FIG. 1 is a graph showing adsorption/desorption of PVP and PVP-coated Ag-nanoparticle to a propylene gas as a function of time.

The nanocomposite membrane of the present invention comprises a nanocomposite, in which silver nanoparticles are uniformly dispersed in a polymer matrix, and a porous membrane supporting the nanocomposite.

The nanocomposite membrane constructed in accordance with the present invention is characterized in that the membrane comprises a neutral Ag-particle having a nano-size as an olefin carrier, which has not been used before as a carrier.

The present invention is described below in detail.

The membrane of the present invention shows superior long-term operation performance characteristics over a conventional membrane employing a metal ion such as a silver ion as a carrier. This is because the neutral Ag-nanoparticle used as a carrier is chemically stable so as not to cause any problems associated with high reductivity or reactivity with other gases such as S-containing compound, acetylene, hydrogen gas, etc., which generally exist in a hydrocarbon mixture.

In the nanocomposite membrane of the present invention, the neutral Ag-particles are uniformly dispersed in a polymer matrix with the nano scale. The Ag-nanoparticle used in the present invention may be prepared by the conventional method or is commercially available. Further, it is preferable to use the Ag-particle having a size of 500 nm or less.

The Ag-nanoparticles in the membrane selectively and reversibly interact with the double bonds of olefins. Thus, the nanocomposite membrane of the present invention can separate an olefin from an olefin/paraffin mixture with a high selectivity.

The olefin/paraffin mixture, which is to be separated in the present invention, is a mixture comprising olefins and paraffins or other gases. Representative examples of the olefin are ethylene, propylene, butylene, 1,3-butadiene, isobutylene, isoprene, mixtures thereof and the like. Those of the paraffin are methane, ethane, propane, butane, isobutene, mixtures thereof and the like. Further, the representative examples of other gases are oxygen, nitrogen, carbon dioxide, carbon monoxide, hydrogen gas, water, acetylene, mixtures thereof and the like.

Exemplary polymers, which can be used for uniformly dispersing the Ag-nanoparticles in the present invention, include, but not limited to, polyethylene oxide (PEO), polyvinyl pyrrolidone (PVP), poly(2-ethyl-2-oxazoline) (POZ), poly(1-trimethylsilyl-1-propyne) (PTMSP), polydimethylsiloxane (PDMS), poly(ethylene-co-propylene) (EPR), ethylene-propylene-butadiene terpolymer (EPDM), polyacrylate, and mixtures thereof.

The porous supported membrane, which may be employable in the present invention, includes all the membranes having good permeability and sufficient mechanical strength. For example, all the conventional porous polymer membranes and ceramic membranes may be employed. There is no limitation as to the type of supported membrane to be used (e.g., plate, tubular, hollow or other types).

The membrane of the present invention may be prepared by coating the nanocomposite solution, in which Ag-nanoparticles are uniformly dispersed in the polymer, on the surface of the porous supported membrane Specifically, the membrane of the present invention may be prepared by: (i) providing an Ag-nanoparticle coated with a coating agent; (ii) dispersing the surface-coated Ag-nanoparticle in a polymer solution by a simple agitation to obtain a nanocomposite solution; and (iii) coating the nanocomposite solution on the surface of a porous supported membrane and drying the resulting membrane.

In the process of preparing the nanocomposite membrane of the present invention, the surface-coated Ag-nanoparticle is employed to prevent the Ag-nanoparticles from self-assembling, thus resulting in dispersibility enhancement of the Ag-nanoparticles in a polymer matrix. The surface-coated Ag-nanoparticle may be prepared by coating the surface of an Ag-nanoparticle with the coating agent in accordance with any of the conventional procedures (e.g., using a v-ray irradiation or a simple agitation technique), or may be commercially available.

A suitable coating agent that can be used in the present invention is a polymer having a functional group containing, for example, O, N, etc., which is capable of interacting with the Ag-nanoparticle. Representative examples include polyethylene oxide (PEO), polyvinyl pyrrolidone (PVP), poly(2-ethyl-2-oxazoline) (POZ) and the like.

The nanocomposite solution may be obtained in step (ii) by dissolving the surface-coated Ag-nanoparticles in the polymer solution composed of a solvent and a polymer, and then stirring the resulting dispersion. The solvent used in this step includes all the solvents, which are capable of dissolving the polymer and have high miscibility with the surface-coated Ag-nanoparticle without having adverse effects upon the supported membrane. Representative examples include water, ethanol, methanol, acetonitrile and mixtures thereof, etc. The polymer used in this step also should have high miscibility with the surface-coated Ag-nanoparticle and the representative examples thereof are described above.

Further, the coating step (iii) may be carried out via a common coating technique, e.g., a Blade/Knife-, Mayer Bar-, Dip-, or Air Knife-coating method.

It is preferable to maintain the coating thickness of the nanocomposite solution, which is formed on the surface of the supported membrane, after drying it as thin as possible in order to increase the permeability of the membrane. However, if the dried thickness of the nanocomposite layer is too thin, then all the pores of the porous supported membrane may not get covered completely. Alternatively, a puncture may be formed on the membrane due to the difference of the loading pressure during the operation, which causes the deterioration of selectivity. Therefore, it is preferable to maintain the dried thickness of the nanocomposite layer in the range from 0.05 to 10 μm, and more preferably from 0.1 to 3 μm.

The nanocomposite membrane of the present invention has excellent long-term performance characteristics due to the use of an Ag-nanoparticle as a carrier, which is chemically stable. Thus, it can be advantageously used in the separation of olefin from an olefin/paraffin mixture.

The present invention is further described and illustrated in the Examples provided below. However, it should be expressly noted herein that the Examples are not intended to limit the scope of the present invention.

EXAMPLE 1

The degree of adsorption/desorption of Ag-nanoparticle for propylene gas was measured by performing the conventional Quartz Crystal Microbalance (QCM) test. The test was performed for a pure poly(vinyl pyrrolidone) (PVP) and the PVP-coated Ag-nanoparticle in a solid state. The results are shown in FIG. 1. As shown in FIG. 1, the Ag-nanoparticles adsorb and desorb reversibly with propylene, thereby participating directly in the transport of propylene.

EXAMPLE 2

0.2 g of poly(2-ethyl-2-oxazoline) (POZ, $M_w$=500,000, Aldrich Co.) was dissolved in 0.8 g of water to obtain a homogenous and transparent polymer solution (polymer concentration was 20 weight %).

5 weight % of Ag-nanoparticles coated with PVP (PVP: Ag-nanoparticle molar ratio of 0.39:0.61) was dispersed in ethanol and the dispersion was added to the polymer solution. The nanocomposite solution thus obtained was coated on a polysulfone porous membrane (Track etched membrane, 0.1 μm polysulfone, Saehan) using a mayer bar. The thickness of the nanocomposite layer on the membrane was about 1.5 μm based on observing the membrane with a high resolution scanning electron microscope (SEM). The resulting membrane was completely dried in a drying oven at a room temperature for 2 hours and then in a vacuum for further 48 hours.

Further, the POZ membrane as a comparative membrane comprising no Ag-nanoparticle was prepared according to the same method described above.

The separation efficiency of each membrane thus prepared was measured by using a gaseous mixture of propylene/propane (50:50 volume %) at a room temperature. Then, the permiability and composition ratios of the permeated gas were measured with a bubble flowmeter and a gas chromatography, respectively. The results are shown in Table 3 as a unit of GPU [1 GPU=1×10$^{-6}$ cm$^2$ (STP)/cm$^2$·cmHg·sec].

TABLE 1

|  | POZ membrane | | Ag/POZ nanocomposite membrane | |
| --- | --- | --- | --- | --- |
| Pressure (psig) | Mixed gas permeability (GPU) | Mixed gas selectivity (propylene/propane) | Mixed gas permeability (GPU) | Mixed gas selectivity (propylene/propane) |
| 10 | 0.1 | 0.97 | 2.2 | 18.4 |
| 20 | 0.1 | 0.98 | 2.3 | 18.6 |
| 30 | 0.1 | 0.97 | 2.2 | 19.0 |
| 40 | 0.1 | 0.99 | 2.2 | 18.8 |

As shown in Table 1, the nanocomposite membrane of the present invention comprising Ag-nanoparticles shows higher permeability and selectivity than the comparative polymeric membrane at all pressure conditions.

EXAMPLE 3

Several membranes comprising Ag-nanoparticles in various concentrations as shown in Table 2 were prepared. Then, the selectivity and permeability of each membrane were measured according to the same method described in Example 2. The results are shown in Table 2.

TABLE 2

| Concentration of the Ag-nanoparticle (wt %) | Mixed gas permeability (GPU) | Mixed gas selectivity (propylene/propane) |
| --- | --- | --- |
| 5 | 2.2 | 18.8 |
| 10 | 2.1 | 19.5 |
| 20 | 1.9 | 21.4 |
| 30 | 1.6 | 22.6 |

As shown in Table 2, the selectivity of the membrane was increased with the increase of the Ag-nanoparticle concentration, while the permeability decreased.

EXAMPLE 4

The efficiencies for a long-term operation of the membrane prepared in Example 2 and the AgBF$_4$/POZ membrane as a comparative membrane were tested at a room temperature, as follows. The separation efficiency was evaluated by using a gaseous mixture of propylene/propane (50:50 volume %) at 40 psig of upper part pressure and atmospheric pressure (0 psig) of permeation part pressure. Then, the permeability and composition ratio of the permeated gas were measured with a bubble flowmeter and gas chromatography, respectively. The results are shown in Table 3.

TABLE 3

| Time (day) | AgBF$_4$/POZ membrane | | Ag/POZ nanocomposite membrane | |
|---|---|---|---|---|
| | Mixed gas permeability (GPU) | Mixed gas selectivity (propylene/propane) | Mixed gas permeability (GPU) | Mixed gas selectivity (propylene/propane) |
| 0 | 10.8 | 52.0 | 2.2 | 18.8 |
| 1 | 8.7 | 46.4 | 2.2 | 18.9 |
| 2 | 7.3 | 39.3 | 2.3 | 19.1 |
| 3 | 6.8 | 35.9 | 2.2 | 18.9 |
| 4 | 5.6 | 20.5 | 2.2 | 18.7 |
| 8 | 3.8 | 17.0 | 2.2 | 18.9 |
| 10 | 3.5 | 12.0 | 2.3 | 18.9 |
| 12 | 3.2 | 10.5 | 2.2 | 19.0 |
| 14 | 2.9 | 8.1 | 2.2 | 18.9 |

As shown in Table 3, the comparative AgBF$_4$/POZ membrane comprising a silver ion shows a high initial selectivity of 50 or more and a permeability of 10 GPU or more. However, its performance characteristics continuously decrease with time. On the other hand, the Ag/POZ nanocomposite membrane of the present invention comprising a neutral Ag-nanoparticle shows 18 or more selectivity and 2.2 GPU or more permeability, while maintaining high performance characteristics during a long operation time of about 14 days.

EXAMPLE 5

The membrane was prepared according to the same method described in Example 2, except that POZ was replaced with poly(ethylene oxide) (PEO, M$_w$=1×10$^6$, Aldrich Co.). The efficiency for a long-term operation of the membrane was evaluated according to the same method and conditions described in Example 4. The results are shown in Table 4.

TABLE 4

| Time (day) | AgBF$_4$/PEO membrane | | Ag/PEO nanocomposite membrane | |
|---|---|---|---|---|
| | Mixed gas permeability (GPU) | Mixed gas selectivity (propylene/propane) | Mixed gas permeability (GPU) | Mixed gas selectivity (propylene/propane) |
| 0 | 12.5 | 23.5 | 1.8 | 14.8 |
| 1 | 11.8 | 22.8 | 1.8 | 14.9 |
| 2 | 11.5 | 22.2 | 1.7 | 14.6 |
| 3 | 8.8 | 17.5 | 1.8 | 14.4 |
| 4 | 7.2 | 15.5 | 1.9 | 14.9 |
| 8 | 5.8 | 13.6 | 1.9 | 14.7 |
| 10 | 5.4 | 11.4 | 1.8 | 14.5 |
| 12 | 4.3 | 8.5 | 1.8 | 14.9 |
| 14 | 3.2 | 6.4 | 1.9 | 14.6 |

As shown in Table 4, the comparative AgBF$_4$/PEO membrane shows high permeability and selectivity at an initial stage of the operation. However, it shows a decline in permeability and selectivity as the operation time increases. Further, the Ag/PEO nanocomposite membrane of the present invention shows a selectivity of greater than 14 and a permeability of greater than 1.8 GPU, while maintaining high performance characteristics during a long operation time of about 14 days.

EXAMPLE 6

The membrane was prepared according to the same method described in Example 2, except that POZ was replaced with poly(1-trimethylsilyl-1-propyne) (PTMSP, M$_w$=1×10$^6$, Aldrich Co.). The efficiency for a long-term operation of the membrane was measured according to the same method and conditions described in Example 4. The results are shown in Table 5.

TABLE 5

| Time (day) | Ag/PTMSP nanocomposite membrane | |
|---|---|---|
| | Mixed gas permeability (GPU) | Mixed gas selectivity (propylene/propane) |
| 0 | 15.1 | 10.8 |
| 1 | 15.2 | 10.9 |
| 2 | 15.2 | 10.6 |
| 3 | 15.1 | 10.4 |
| 4 | 15.2 | 10.9 |
| 8 | 15.2 | 10.7 |
| 10 | 15.2 | 10.5 |
| 12 | 15.2 | 10.9 |
| 14 | 15.2 | 10.6 |

As shown in Table 5, the nanocomposite membrane of the present invention wherein Ag-nanoparticles are dispersed in PTMSP shows a high permeability of greater than 15 GPU and a selectivity of greater than 10, while maintaining its high performance characteristics during a long operation time of about 14 days.

EXAMPLE 7

The membrane was prepared according to the same method described in Example 2, except that POZ was replaced with poly(dimethyl siloxane) (PDMS, M$_w$ 48,000, Dow Corning). The efficiency for a long-term operation of the membrane was evaluated according to the same method and conditions described in Example 4. The results are shown in Table 6.

TABLE 6

Ag/PDMS nanocomposite membrane

| Time (day) | Mixed gas permeability (GPU) | Mixed gas selectivity (propylene/propane) |
|---|---|---|
| 0 | 8.3 | 30.2 |
| 1 | 8.4 | 31.0 |
| 2 | 8.4 | 30.8 |
| 3 | 8.3 | 30.5 |
| 4 | 8.3 | 30.5 |
| 8 | 8.3 | 31.4 |
| 10 | 8.4 | 30.2 |
| 12 | 8.4 | 30.5 |
| 14 | 8.3 | 30.6 |

As shown in Table 6, the nanocomposite membrane of the present invention wherein Ag-nanoparticles are dispersed in PDMS shows a high permeability of greater than 8 GPU and a selectivity of greater than 30, while maintaining its high performance characteristics during a long operation time of about 14 days.

EXAMPLE 8

The membrane was prepared according to the same method described in Example 2, except that POZ was replaced with poly(ethylene-co-propylene) (EPR, $M_w$=170,000, Aldrich Co.). The efficiency for a long operation of the membrane was evaluated according to the same method and conditions described in Example 4. The results are shown in Table 7.

TABLE 7

Ag/EPR nanocomposite membrane

| Time (day) | Mixed gas permeability (GPU) | Mixed gas selectivity (propylene/propane) |
|---|---|---|
| 0 | 7.2 | 25.2 |
| 1 | 7.2 | 25.9 |
| 2 | 7.4 | 26.8 |
| 3 | 7.4 | 25.7 |
| 4 | 7.2 | 25.6 |
| 8 | 7.3 | 25.5 |
| 10 | 7.4 | 25.6 |
| 12 | 7.4 | 25.4 |
| 14 | 7.3 | 25.7 |

As shown in Table 7, the nanocomposite membrane of the present invention wherein Ag-nanoparticles are dispersed in EPR shows a high permeability of greater than 7 GPU and a selectivity of greater than 25, while maintaining its high performance characteristics during a long operation time of about 14 days.

EXAMPLE 9

The membrane was prepared according to the same method described in Example 2, except that POZ was replaced with ethylene-propylene-butadiene terpolymer (EPDM, $M_w$=310,000, Exxon Mobil Chemical Co.). The efficiency for a long operation of the membrane was evaluated according to the same method and conditions described in Example 4. The results are shown in Table 8.

TABLE 8

Ag/EPDM nanocomposite membrane

| Time (day) | Mixed gas permeability (GPU) | Mixed gas selectivity (propylene/propane) |
|---|---|---|
| 0 | 8.1 | 20.3 |
| 1 | 8.2 | 20.8 |
| 2 | 8.2 | 20.5 |
| 3 | 8.3 | 20.7 |
| 4 | 8.2 | 20.6 |
| 8 | 8.3 | 20.5 |
| 10 | 8.4 | 20.6 |
| 12 | 8.4 | 20.5 |
| 14 | 8.3 | 20.5 |

As shown in Table 8, the nanocomposite membrane of the present invention wherein Ag-nanoparticles are dispersed in EPDM shows a high permeability of greater than 8 GPU and a selectivity of greater than 20, while maintaining its high performance characteristics during a long operation time of about 14 days.

While the invention has been described with respect to the above specific embodiments, it should be recognized that various modifications and changes may be made to the invention by those skilled in the art which also fall within the scope of the invention as defined by the appended claims.

What is claimed is:

1. A nanocomposite membrane for separating an olefin from an olefin/paraffin mixture, comprising (i) a nanocomposite comprising surface-coated Ag-nanoparticles and a polymer, wherein the surface-coated Ag-nanoparticles are coated with a coating agent, and (ii) a porous membrane for supporting the nanocomposite.

2. The nanocomposite membrane of claim 1, wherein the polymer is selected from the group consisting of polyethylene oxide (PEO), polyvinyl pyrrolidone (PVP), poly(2-ethyl-2-oxazoline) (POZ), poly( 1 -trimethylsilyl- 1 -propyne) (PT-MSP), polydimethylsiloxane (PDMS), poly(ethylene-co-propylene) (EPR), ethylene-propylene-butadiene terpolymer (EPDM), polyacrylate, and mixtures thereof.

3. The nanocomposite membrane of claim 1, wherein the Ag-nanoparticle of said surface-coated Ag-nanoparticle has a particle size of 500 nm or less.

4. The nanocomposite membrane of claim 1, wherein the olefin/parrafin mixture is a mixture comprising at least one olefin and at least one paraffin or another gas.

5. The nanocomposite membrane of claim 4, wherein the olefin is selected from the group consisting of ethylene, propylene, butylene, 1,3-butadiene, isobutylene, isoprene and mixtures thereof, and wherein the paraffin is selected from the group consisting of methane, ethane, propane, butane, isobutene and mixtures thereof, and wherein the another gas is selected from the group consisting of oxygen, nitrogen, carbon dioxide, carbon monoxide, hydrogen gas, water and mixtures thereof.

6. A process for preparing the nanocomposite membrane according to any one of claims 1 to 5, comprising the steps of: (i) coating a Ag-nanoparticle with a coating agent, thereby providing a surface-coated Ag-nanoparticle; (ii) dispersing the surface-coated Ag-nanoparticle in a polymer solution to obtain a nanocomposite solution; and (iii) coating the nanocomposite solution on a porous support.

7. The process of claim 6, wherein the coating agent is selected from the group consisting of polyethylene oxide (PEO), polyvinyl pyrrolidone (PVP) and poly(2-ethyl-2-oxazoline) (POZ).

8. The process of claim 6, wherein the polymer solution is composed of the polymer selected from the group consisting of polyethylene oxide (PEO), polyvinyl pyrrolidone (PVP), poly(2-ethyl-2-oxazoline) (POZ), poly(1-trimethylsilyl-1-propyne) (PTMSP), polydimethylsiloxane (PDMS), poly(ethylene-co-propylene) (EPR), ethylene-propylene-butadiene terpolymer (EPDM), polyacrylate and mixtures thereof, and wherein the polymer solution is further composed of the solvent selected from the group consisting of water, ethanol, methanol, acetonitrile and mixtures thereof.

* * * * *